United States Patent
Lorach et al.

(10) Patent No.: US 9,987,167 B2
(45) Date of Patent: Jun. 5, 2018

(54) METHOD AND DEVICE FOR CONTROLLING A DEVICE FOR AIDING VISION

(75) Inventors: Henri Lorach, Paris (FR); Ryad Benosman, Paris (FR); Jose Sahel, Paris (FR); Srege Picaud, Avon (FR)

(73) Assignees: UNIVERSITE PIERRE ET MARIE CURIE (PARIS 6), Paris (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 430 days.

(21) Appl. No.: 14/115,983

(22) PCT Filed: May 11, 2012

(86) PCT No.: PCT/FR2012/051052
§ 371 (c)(1),
(2), (4) Date: Nov. 6, 2013

(87) PCT Pub. No.: WO2012/153073
PCT Pub. Date: Nov. 15, 2012

(65) Prior Publication Data
US 2014/0085447 A1    Mar. 27, 2014

(30) Foreign Application Priority Data
May 12, 2011    (FR) ...................... 11 54116

(51) Int. Cl.
*H04N 7/18*    (2006.01)
*A61F 9/08*    (2006.01)
(Continued)

(52) U.S. Cl.
CPC .............. *A61F 9/08* (2013.01); *A61N 1/0543* (2013.01); *A61N 1/36046* (2013.01);
(Continued)

(58) Field of Classification Search
CPC ..... A61N 1/36046; A61N 1/0543; A61F 9/08; G06K 9/4623; G09B 21/008
(Continued)

(56) References Cited

U.S. PATENT DOCUMENTS 7,728,269 B2    6/2010    Lichtsteiner et al.
8,428,739 B2    4/2013    Ahuja et al.
(Continued)

OTHER PUBLICATIONS

Sivaprakasam, Mohanasankar, et al. "A variable range bi-phasic current stimulus driver circuitry for an implantable retinal prosthetic device." Solid-State Circuits, IEEE Journal of 40.3 (2005): 763-771.*
(Continued)

*Primary Examiner* — Tat C Chio
*Assistant Examiner* — Fabio S Lima
(74) *Attorney, Agent, or Firm* — Frost Brown Todd LLC (57) ABSTRACT

An input signal (f) representative of a scene to be viewed comprises, for each pixel of a matrix of pixels, an event-based asynchronous-signal sequence obtained as a function of variations of light relating to the pixel in the scene. This input signal is transformed spatially within the matrix of pixels and temporally along the signal sequences to generate respective control signals (S) for pixel zones of a device for aiding vision (20).

19 Claims, 7 Drawing Sheets

(51) Int. Cl.
| | | |
|---|---|---|
| A61N 1/05 | (2006.01) | |
| A61N 1/36 | (2006.01) | |
| G09B 21/00 | (2006.01) | |
| G06K 9/46 | (2006.01) | |
| G06N 3/063 | (2006.01) | |

(52) U.S. Cl.
CPC ......... G06K 9/4623 (2013.01); G09B 21/008 (2013.01); G06N 3/063 (2013.01)

(58) Field of Classification Search
USPC .......................................................... 348/62
See application file for complete search history.

(56) References Cited

U.S. PATENT DOCUMENTS

| | | | | |
|---|---|---|---|---|
| 2007/0299484 | A1* | 12/2007 | Greenberg ......... | A61N 1/36046 607/54 |
| 2009/0112287 | A1 | 4/2009 | Greenberg et al. | |
| 2009/0118792 | A1 | 5/2009 | McClure et al. | |
| 2010/0036457 | A1* | 2/2010 | Sarpeshkar .......... | G09B 21/008 607/53 |
| 2010/0067825 | A1 | 3/2010 | Zhou et al. | |
| 2010/0182468 | A1 | 7/2010 | Posch et al. | |
| 2013/0096660 | A1 | 4/2013 | Lorach et al. | |

OTHER PUBLICATIONS

Liu, Wentai, et al. "Image processing and interface for retinal visual prostheses." Circuits and Systems, 2005. ISCAS 2005. IEEE International Symposium on. IEEE, 2005.*

Liu, Wentai, et al. "A neuro-stimulus chip with telemetry unit for retinal prosthetic device." Solid-State Circuits, IEEE Journal of 35.10 (2000): 1487-1497.*

Liu et al. "Neuromorphic sensory systems." Current opinion in neurobiology 20.3 (2010): 288-295.*

Lin et al. "A neuromorphic chip that imitates the on brisk transient ganglion cell set in the retinas of rabbits." Sensors Journal, IEEE 7.9 (2007): 1248-1261.*

Thiel et al. "The temporal structure of transient On/Off ganglion cell responses and its relation to intra-retinal processing." Journal of computational neuroscience 21.2 (2006): 131-151.*

Lichtsteiner, Patrick, Christoph Posch, and Tobi Delbruck. "A 128x 128 120 dB 15 μs latency asynchronous temporal contrast vision sensor." IEEE journal of solid-state circuits 43.2 (2008): 566-576.*

"Video encoding, SoC development, and TI's DSP architecture." EEtimes. N.p., May 26, 2006. Web. May 3, 2017. <http://www.eetimes.com/document.asp?doc_id=1273628>.*

International Search Report dated Aug. 9, 2012 for Application No. PCT/FR2012/051052 with English Translation.

Written Opinion dated Aug. 9, 2012 for Application No. PCT/FR2012/051052 with English Translation.

International Preliminary Report on Patentability dated Nov. 12, 2013 for Application No. PCT/FR2012/051052 with English Translation.

Gollisch, T., et al., "Rapid Neural Coding in the Retina with Relative Spike Latencies", Science, vol. 319, Feb. 2008, pp. 1108-1111.

Lichtsteiner, P., et al., "A 128×128 120 dB 15 μs Latency Asynchronous Temporal Contrast Vision Sensor", IEEE Journal of Solid-State Circuits, vol. 43, No. 2, Feb. 2008, pp. 566-576.

Lin, Li-Ju, et al., "A Neuromorphic Chip That Imitates the On Brisk Transient Ganglion Cell Set in the Retinas of Rabbits", IEEE Sensors Journal, IEEE Service Center, New York, NY, US, vol. 7, No. 9, Sep. 1, 2007, pp. 1248-1261. XP0111876666.

Liu, S.C., et al., "Neuromorphic sensory systems", Current Opinion in Neurobiology, London, GB, vol. 20, No. 3, Jun. 1, 2010, pp. 228-295. XP027079056.

Roska, B., et al., "Parallel Processing in Retinal Ganglion Cells: How Intergration of Space-Time Patterns of Excitation and Inhibition Form the Spiking Output", Journal of Neurophysiology, vol. 95, No. 6, 2006, pp. 3810-3822.

Schwarz, Markus, et al., "Single-Chip CMOS Image Sensors for a retina Implant System", IEEE Transactions on Circuits and Systems II: Analog and Digitalsignal Processing, Institute of Electrical and Electronics Engineers Inc., New York, NY, USA, vol. 46, No. 7, Jul. 1, 1999. XP011013088.

Thiel, Andreas, et al., "The temporal structure of transient On/Off ganglion cell responses and its relation to intra-retinal processing", Journal of Computational Neuroscience, Klumer Academic Publishers, BO, vol. 21, No. 2, May 26, 2006, pp. 131-151. XP019398617.

Zaghloul, K., et al., "Optic Nerve Signals in a Neuromorphic Chip I: Outer and Timer Retina Models", IEEE Transactions on Biomedical Engineering, IEE Service Center, Piscataway, NJ, USA, vol. 51, No. 4, Apr. 1, 2004, pp. 657-666. XP011109270.

* cited by examiner

METHOD AND DEVICE FOR CONTROLLING A DEVICE FOR AIDING VISION

The present invention relates to the field of devices for aiding vision, and more specifically to controlling prostheses or orthoses to provide visual information to the people who wear them.

Vision rehabilitation with visual prostheses aims to stimulate neurons along the visual pathway between the retina and the brain in order to evoke perception in the visually challenged. A visual prosthesis is implanted near nerve cells where it applies an electrical field that is spatially and temporally modulated. The electrical field is locally applied in pixel zones arranged in a matrix. It induces electrical potentials in the neuronal membranes that receive its influence. The still-functional cells of the retina or visual cortex can be stimulated even if the photoreceptors and other retinal cells are no longer functional.

Existing approaches target different areas of the vision system. Subretinal implants stimulate bipolar cells of the retina, while epiretinal implants stimulate ganglion cells that are connected to the brain via the optic nerve. Both strategies attempt to use the retinal cells which remain after degeneration of the photoreceptor cells. Another approach uses cortical implants that directly stimulate the visual cortex and can be used even in cases where the optic nerve is damaged. These three strategies have been tested in clinical trials and have shown that they can evoke phosphenes and enable shape recognition and in some cases letter recognition.

Orthoses are designed to present preprocessed and therefore simplified visual information to retinal areas that are still functional, in order to provide missing visual information. This information may be missing because of a corresponding scotoma or may be normally inaccessible due to its complexity, size, or contrast (enhanced vision).

Devices for aiding vision (prostheses or orthoses serving as visual aid devices) are supplied signals obtained by treating signals from a light capturing system. Conventional strategies include capturing light as images or video frames regularly spaced over time. This sampling method, used for example in U.S. 2010/0067825 A1, poses several difficulties.

Image processing which can involve intense computation, such as saliency extraction or contour extraction, is applied to the images to define an activation scheme for the visual aid device. The various stimulation strategies adopted have not yielded satisfactory results to date. The limitations of this method are due to the low dynamic range of the sensor, which yields an image every 33 ms at best. On the other hand, use of the faster CCD (charge-coupled device) cameras is incompatible with the complexity of image processing algorithms and is not suitable for a portable system.

Reproducing the dynamic characteristics of the visual system requires a very short response time. It has been shown that the mammalian brain manages to extract certain features of the visual field within a few tens of milliseconds. The processing delay attributable to the retina is about 50 ms. When sampling image by image, it is necessary to collect several images to observe temporal gradients for information gathering purposes. The 50 ms time the retina requires for modeling is already exceeded if two images are captured at 40 Hz. Therefore, precise real-time extraction of characteristics by the retina theoretically requires a sampling frequency of above 60 Hz to calculate second order time derivatives, process the signal, and extract the characteristics.

In addition, the basic stimuli must be temporally positioned with a precision of a few milliseconds due to the very rapid dynamics of the processing of visual information (see "Rapid Neural Coding in the Retina with Relative Spike Latencies", Gollisch T. et al., Science, Vol. 319, February 2008, p. 1108-1111). This requirement cannot be met by frame-by-frame capture systems having realistic sampling frequencies.

A need therefore exists for techniques which allow appropriately controlling visual aid devices.

A method is proposed for controlling a visual aid device, which comprises:
  receiving an input signal representative of a scene to be viewed, the input signal comprising, for each pixel in a matrix of pixels, an event-based asynchronous signal sequence obtained as a function of variations of light relating to the pixel in the scene;
  transforming the input signal spatially within the matrix of pixels and temporally along the signal sequences to generate respective control signals for pixel zones of the visual aid device; and
  applying the control signals to the visual aid device.

There are many advantages to using asynchronous signals to construct the control signals for the visual aid device. These signals are not sampled over time at a predefined clock rate, unlike the clock for the frames in a conventional video signal. They provide what is referred to as an address-event representation (AER) of a scene to be viewed. Corresponding to each pixel, there is an event-based signal sequence, i.e. dependent on the variations in light intensity corresponding to this pixel. In an exemplary embodiment, the event-based asynchronous signal sequence for a pixel comprises a sequence of positive or negative pulses temporally positioned as a function of the light variations relating to this pixel. This type of acquisition reproduces the continuous light acquisition of retinal photoreceptors. It takes advantage of the high degree of temporal redundancy in the field of vision. Therefore:
  there is no need to repeat over time the substantially constant light levels seen by the majority of pixels, the way a conventional videocamera does at a given frame rate;
  it is possible to recognize local variations in light quickly and with accurate temporal positioning, without being limited by an inter-frame period.

The asynchronous signal sequences are transformed spatially and temporally to provide information that is useful to the visual orthoses or prostheses. Several approaches can be adopted for this transformation. In general, it will be necessary to adapt the control, and therefore the parameters of the signal transformation, to wearer requirements.

One approach is based on a model of the behavior of different types of retinal cells.

The transformation of the input signal to generate the control signals may include:
  obtaining a first signal resulting from: two spatial filtering operations with filtering kernels of different sizes, calculation of a difference between the results of the two spatial filtering operations, and a temporal filtering operation on the difference; and
  obtaining a second signal of zero value if the first signal has a value of a specific sign, and of the same absolute value as the first signal otherwise.

The use of filter kernels of different sizes can be considered as taking into account the behavior of retinal photoreceptors and horizontal cells, the latter typically having a larger radius of interaction than photoreceptors. The second signal reproducing the positive or negative portion of the first signal can be viewed as being the signal created by a bipolar cell. The polarity of the calculated difference distinguishes between 'ON' bipolar cells and 'OFF' bipolar cells. Different sets of parameters for spatial and/or temporal filtering can also distinguish between behaviors of different types of bipolar cells, given that there are at least ten different types of bipolar cells.

This type of transformation is suitable for subretinal visual prostheses, as the control signals applied to the visual prosthesis are then generated from the second signal. It is also suitable for an orthosis containing an array of light-emitting elements.

It is also possible to continue the transformation beyond the obtaining of these second signals. In one embodiment, at least a first excitatory signal and a first inhibitory signal are obtained with respective time constants for the temporal filtering operation on the difference, then at least a second excitatory signal and a second inhibitory signal are respectively obtained from the first excitatory and inhibitory signals. The excitatory and inhibitory channels simulated in this manner correspond to bipolar cells which can provide excitatory input and inhibitory input to a ganglion cell via amacrine cells. The transformation of the input signal to generate the control signals then comprises, after these second signals are obtained:

obtaining a third signal resulting from a spatial filtering operation on the difference between the second excitatory signal and an inhibitory component derived from the second inhibitory signal; and when the third signal for a given pixel zone of the visual aid device exceeds a predetermined threshold value, inserting a pulse into the control signal intended for said pixel zone and resetting the third signal for said pixel zone to zero.

In the model, the derivation of the inhibitory component from the second inhibitory signal is attributable to amacrine cells, and may include the application of a predetermined delay and a spatial filtering operation.

A control signal generated from a third signal obtained in this way may, for some patients, be suitable for a visual prosthesis implanted in an epiretinal or cortical position or on the lateral geniculate nucleus.

An interesting possibility which allows reproducing the behavior of a direction-selective ganglion cell is to use an off-center filtering kernel in the spatial filtering operation involved in the derivation of the inhibitory component. This spatial offset of the filtering kernel, combined with the delay induced by the amacrine cells, results in the response being sensitive to the direction of movement of the stimuli.

Some ganglion cells can be excited in a combined manner from bipolar cells of different types. To take this into account, second excitatory and inhibitory signals for a first channel and for a second channel can be obtained with temporal filtering operations at respective time constants. The transformation of the input signal to generate the control signals then comprises, after these second signals are obtained:

obtaining a third signal resulting from a spatial filtering operation on the difference between a linear combination of the second excitatory signals for the first and second channels and an inhibitory component derived from the second inhibitory signals for the first and second channels; and when the third signal for a given pixel zone of the visual prosthesis exceeds a given threshold value, inserting a pulse into the control signal for this pixel zone and resetting the third signal for the pixel zone to zero.

In the model, the derivation of the inhibitory component from the second inhibitory signals is attributable to amacrine cells of a different type than mentioned above, and may include the application of respective delays to the second inhibitory signals for the first and second channels, a spatial filtering operation on the delayed second inhibitory signals, and calculation of a linear combination of delayed and filtered second inhibitory signals.

A control signal generated from a third signal obtained in this way may, for some patients, be suitable for a visual prosthesis implanted in an epiretinal or cortical position or on the lateral geniculate nucleus. It may also be suitable for an orthosis comprising an array of light-emitting elements.

Different models, more or less based on the known behavior of nerve cells, can serve as a reference when developing the specific transformation to be applied to the control signals for the prosthesis of a given patient. Psychophysical tests can be used to select the most appropriate transformation for a given individual.

It is still possible to develop this transformation without reference to a phenomenological model, for example using an artificial neural network.

Another aspect of the invention relates to a device for processing signals for controlling a visual aid device, comprising: an input for receiving an input signal representative of a scene to be viewed, the input signal comprising, for each pixel in a matrix of pixels, an event-based asynchronous signal sequence obtained as a function of variations of light relating to the pixel in the scene; an output for supplying the control signals for the visual aid device; and a processing circuit for generating the control signals according to a method as defined above.

Other features and advantages of the invention will be apparent from the following description of some non-limiting exemplary embodiments, with reference to the accompanying drawings in which.

The role of the retina is to encode the luminous flux it receives into a sequence of action potentials transmitted to the brain via the optic nerve. The phototransduction cascade and the interactions between different cell types within the retina result in a complex system of ganglion cell activation. Estimates predict dozens of types of ganglion cell responses, depending on their morphology and physiology.

Despite the variety in the types of responses observed, it has been shown that a temporal precision of a few milliseconds in the sequence of action potentials is essential to proper interpretation of this information by the brain. It is necessary to attempt a faithful reproduction of the dynamics of retinal cells when considering prosthetic treatment of blindness. The basic principle of this treatment is electrical stimulation of retinal cells in cases of degenerative diseases of the photoreceptors.

In this application, the equipment used (FIG. 1) comprises a light capturing device 10 having a group of photosensitive elements arranged in a matrix of pixels, and a prosthesis 20 installed for example on the retina. Cortical implantation of the prosthesis 20 is also possible. A processing unit 30 converts the input signal f from the light capturing unit 10 into a set of control signals S for the respective pixel zones of the prosthesis 20. To apply these control signals S to the prosthesis 20, they are converted into analog electric potentials by a driver unit 40 which sends these potentials to the electrodes of the prosthesis.

Figure 1:
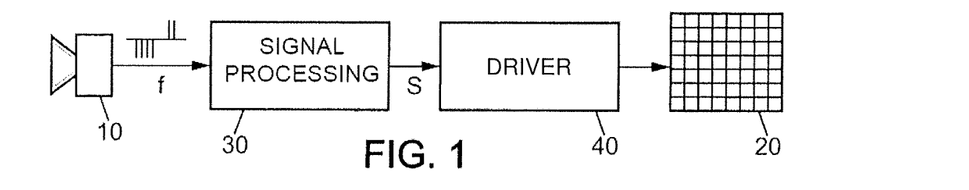
FIG. 1 is a block diagram of example equipment for stimulating the visual system of a patient with impaired vision.

For example, the prosthesis 20 may be of the type described in patent application FR 10 53381 filed on 30 Apr. 2010. Its pixel zones each include a pair of electrodes for locally applying a difference in potential which stimulates the nerve cells subjected to the electrical field this induces. One of the two electrodes may be part of a ground plane that is common to at least some of the pixel zones. The pixel zones of the prosthesis 20 have a spatial density which does not need to match the spatial resolution of the pixel matrix of the light capturing unit 10.

The processing unit 30 which supplies the control signals S works with digital signals. It can be implemented by programming an appropriate processor. In practice, a hardware implementation of the signal processing unit 30 using dedicated logic circuits may be preferred for the industrialization of the equipment.

For each pixel of the matrix, the unit 10 creates an event-based asynchronous signal sequence from the light variations experienced by the pixel in the scene appearing in the field of view of the device. This type of asynchronous photosensitive device can approach the physiological response of the retina and thus produce a suitable control scheme. It is hereinafter referred to by the acronym DVS (dynamic vision sensor).

Figure 2A:
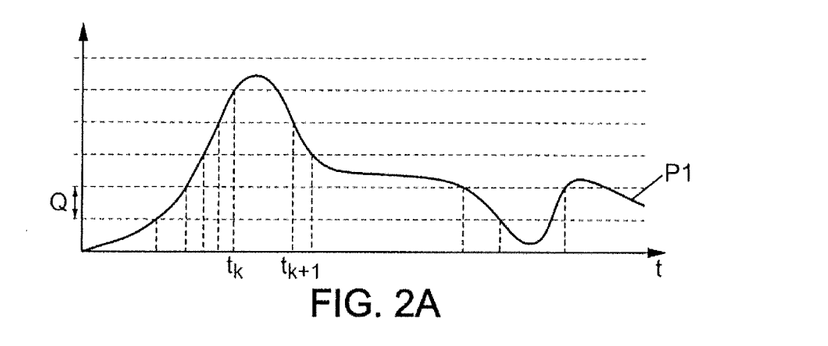
FIG. 2A is a diagram showing an example of a light intensity profile for a pixel of an asynchronous sensor.
Figure 2B:
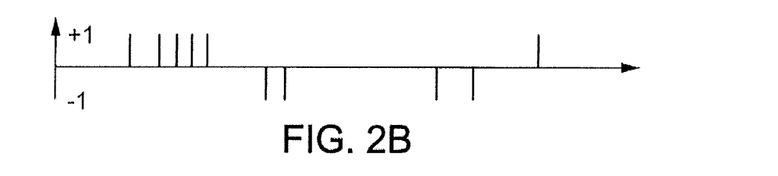
FIG. 2B shows an example of a signal delivered by the asynchronous sensor in response to the intensity profile of FIG. 2A.
Figure 2C:
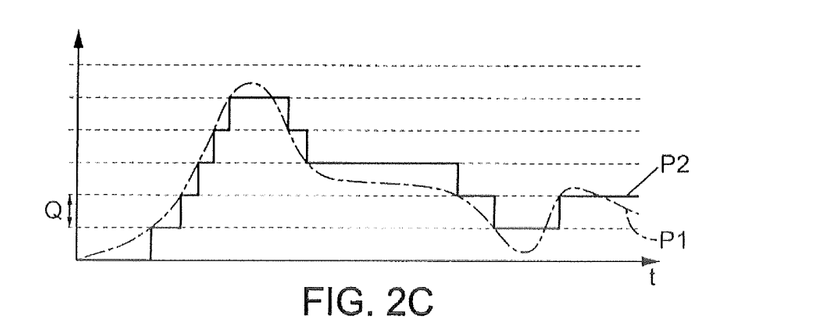
FIG. 2C illustrates the reconstruction of the intensity profile from the signal of FIG. 2B.

The principle of acquisition by this asynchronous sensor is shown in FIGS. 2A-C. The information consists of a succession of times $t_k$ (k=0, 1, 2, ...) at which an activation threshold Q is reached. FIG. 2A shows an example of a light intensity profile P1 as experienced by a pixel in the DVS matrix. Whenever the intensity increases by an amount equal to the activation threshold Q from what it was at time $t_k$, a new time $t_{k+1}$ is identified and a positive line (level+1 in FIG. 2B) is emitted at this time $t_{k+1}$. Symmetrically, whenever the intensity of the pixel decreases by the amount Q from what it was at time $t_{k'}$, a new time $t_{k'+1}$ is identified and a negative line (level −1 in FIG. 2B) is emitted at this time $t_{k'+1}$. The sequence of asynchronous signals for the pixel then consists of a succession of positive and negative lines or pulses temporally positioned at time $t_k$ according to the light profile for the pixel. These lines can be represented mathematically by positive or negative Dirac spikes each characterized by an emission time $t_k$ and a sign bit. The output from the DVS 10 is thus in the form of an address-event representation (AER). FIG. 2C shows the intensity profile P2 that can be reconstructed as an approximation of profile P1 by integrating the asynchronous signal from FIG. 2B over time.

Figure 3A:
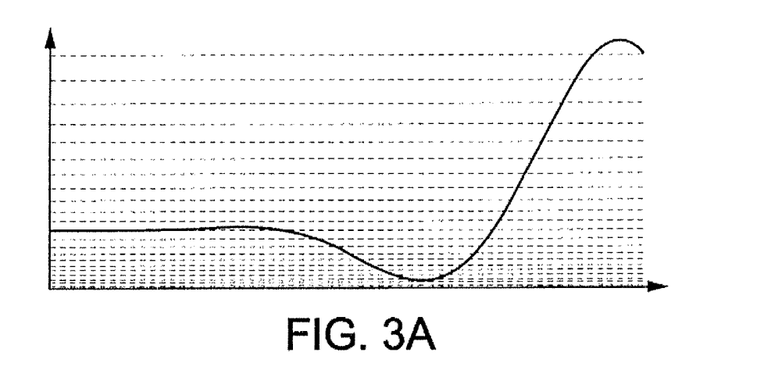
FIGS. 3A-B are diagrams similar to those in FIGS. 2A-B, illustrating a mode of light acquisition usable in another embodiment of the method.
Figure 3B:
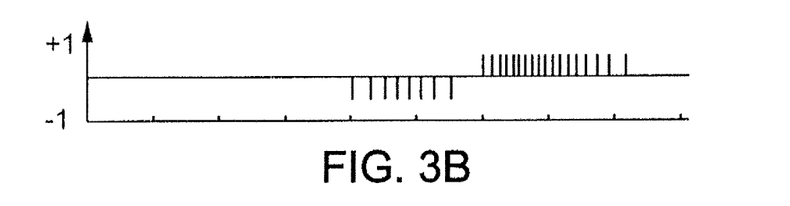

The activation threshold Q may be fixed, as is the case in FIGS. 2A-C, or adapted to the light intensity, as is the case in FIGS. 3A-B. For example, the threshold ±Q can be compared with variations of the logarithm of the light intensity for generating a ±1 event.

For example, the DVS 10 may be of the type described in "A 128×128 120 dB 15 µs Latency Asynchronous Temporal Contrast Vision Sensor", P. Lichtsteiner et al., IEEE Journal of Solid-State Circuits, Vol. 43, No. 2, February 2008, p. 566-576, or patent application US 2008/0135731 A1.

The dynamics of the retina (minimum time of a few milliseconds between action potentials) can be adequately reproduced with a DVS of this type. The performance is certainly much higher than can be achieved with a conventional video camera with a realistic sampling frequency.

It should be noted that the form of the asynchronous signal delivered for a pixel by the DVS 10, which constitutes the input signal to the processing unit 30, may differ by a succession of Dirac spikes, the events represented possibly having any temporal width or amplitude or waveform in this event-based asynchronous signal.

On the other hand, the input signal is not necessarily obtained from a light detection device. It could also be a synthesized AER signal.

In order to stimulate the retinal cells effectively, not only should there be sufficient acquisition dynamics but also the ability to process the acquired signal in a meaningful way. Each type of cell in the visual system has its own activation scheme. For example, some ganglion cells respond preferentially to a given direction, a movement, or a contrast. These properties arise from the retinal network connectivity. In the case of epiretinal prostheses, this connectivity should be reproduced in order to obtain an appropriate stimulation timing.

One approach is to train an artificial neural network with physiological data to link the activity of each type of ganglion cell with the signal from the DVS. The signal from the different pixels of the DVS is introduced into a neural network which integrates the inputs to predict the activity of the ganglion cell. Using known algorithms, the weights involved in the artificial network connections are adjusted until convergence of the prediction with an actual measured activity. The temporal accuracy achieved through such acquisition and filtering can produce an asynchronous stimulation of the retina that is relevant from a physiological point of view.

Another approach is to refer to a model of retinal nerve cell behavior when designing the signal processing performed by the unit 30.

Figure 4:
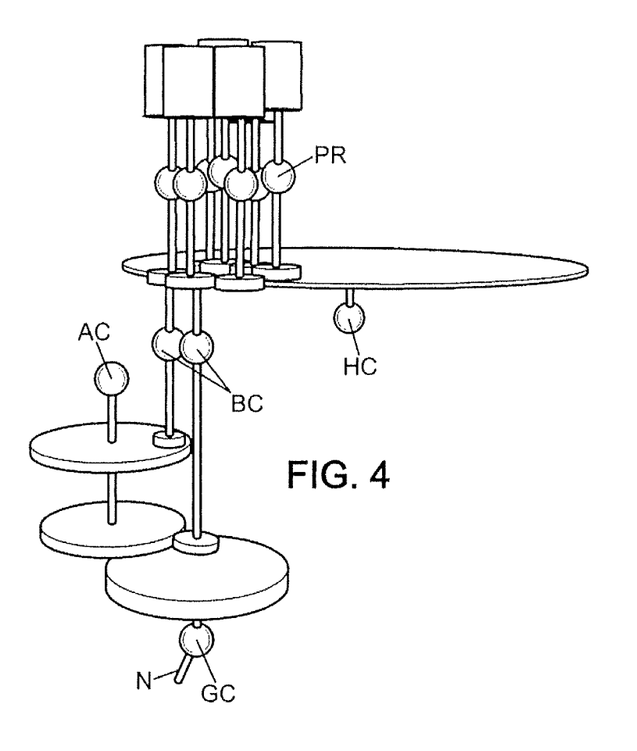
FIG. 4 is a schematic representation of different categories of retinal nerve cells.

The model can be based on a general structure of the retina such as the one represented schematically in FIG. 4. In this model, spatial and/or temporal convolutions are performed at each cellular level. Bipolar cells (BC") perform a non-linear transduction of either the positive or the negative part of the signal from the photoreceptors (PR) after delayed inhibition by the horizontal cells (HC). Some bipolar cells activate 'ON' channels in response to positive stimuli, while others activate 'OFF' channels in response to negative stimuli. Amacrine cells (AC) can introduce interactions between the 'ON' and/or 'OFF' channels with delayed inhibition. This inhibition may also introduce spatial gradients in the case of a time-shifted inhibition. Ganglion cells (GC) receive excitation originating from bipolar cells of the 'ON' and/or 'OFF' channels and inhibition originating from amacrine cells, and behave like neurons performing leaky integration and emitting action potentials ("spikes") to the optic nerve N.

Figure 5:
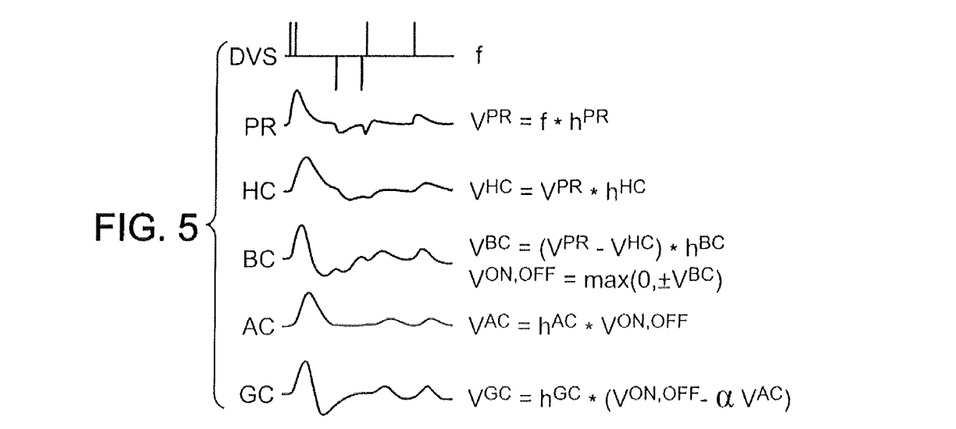
FIG. 5 is a diagram illustrating the responses of several types of retinal cells for a model.

This processing is summarized in FIG. 5. A cell type can be considered as performing a convolution of an input signal $V=V(x, y, t)$ by means of a convolution kernel $h=h(x, y, t)$ having a spatial component, for example Gaussian with a standard deviation representing a radius r of interaction of the cells, and a temporal component with a time constant T. A possible form of the convolution kernel is as follows:

$$h(x, y, t) = \frac{t-D}{\tau^2} \cdot \exp\left[-\frac{t-D}{\tau}\right] \cdot \frac{1}{2\pi r^2} \cdot \exp\left[-\frac{(x-x_0)^2 + (y-y_0)^2}{2r^2}\right] \quad (1)$$

where:
x, y indicate the positions in the two spatial directions;
t indicates the time;
D indicates a delay parameter which may intervene (D≠0) for several types of cells, particularly amacrine cells;
$x_0$, $y_0$ indicate spatial offset parameters which may intervene ($x_0 \neq 0$ and/or $y_0 \neq 0$) for several types of cells, particularly amacrine cells.

In FIG. 5, the first row represents the sequence of positive and negative pulses that form the signal f=f(x, y, t) issuing from the DVS 10 for a pixel at position (x, y) in the input matrix. The processing by the photoreceptors consists of applying convolution kernel $h^{PR}$ to the input signal f. The processing by the horizontal cells consists of applying convolution kernel $h^{HC}$ to signal $V^{PR}$ issuing from the photoreceptors, to form signal $V^{HC}$. The bipolar cells apply convolution kernel $h^{BC}$ to the difference ($V^{PR}-V^{HC}$) to form signal $V^{BC}$ of which only the positive part is retained in the case of an 'ON' channel ($V^{ON}=\max\{0, V^{BC}\}$) and only the negative part is retained in the case of an 'OFF' channel ($V^{OFF}=\max\{0, -V^{BC}\}$). The parameters τ, r are differentiated for kernels $h^{PR}$, $h^{HC}$, $h^{BC}$. For different types of bipolar cells to be modeled, different sets of parameters τ, r are provided whose values can be determined separately.

Figure 6:
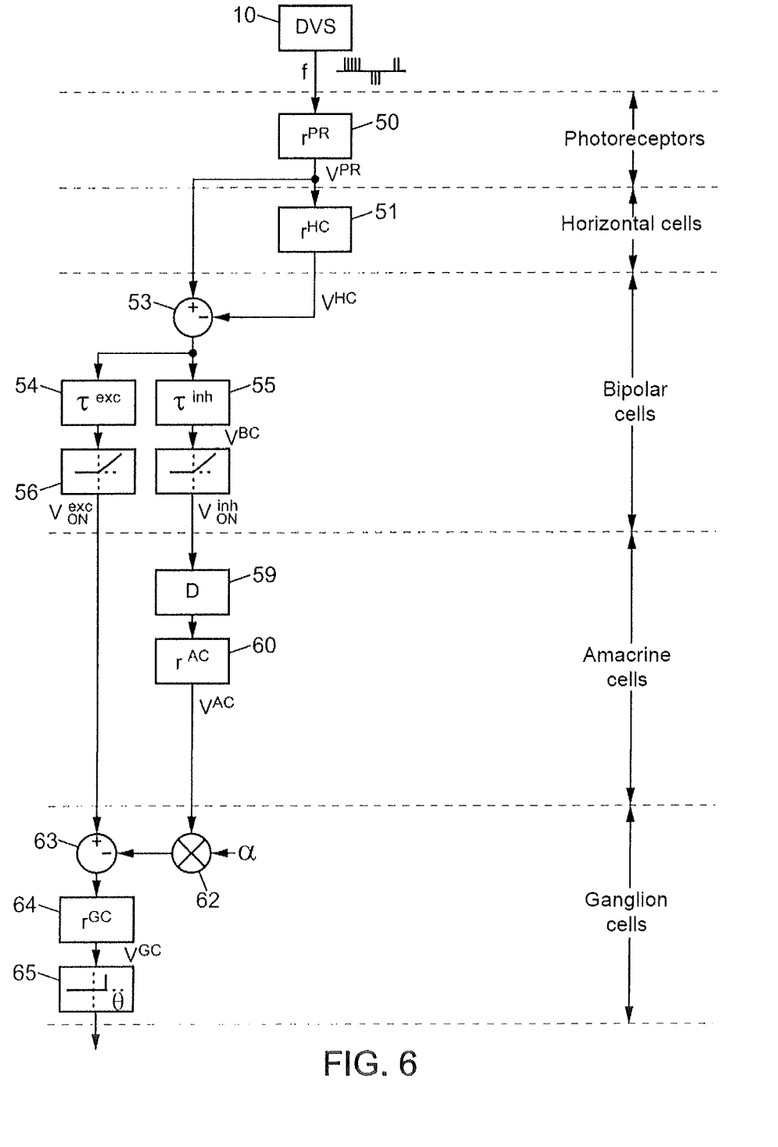
FIGS. 6-9 are diagrams showing the processing that can be applied in several exemplary embodiments of the method.

Due to the linearity of the operations performed until the modeling of the bipolar cells, it is possible, in the example represented in FIG. 6, to perform only spatial convolutions 50, 51 for the photoreceptors and horizontal cells (kernels $h^{PR}$, $h^{HC}$ having radii of interaction $r^{PR}$, $r^{HC}$) and a simply temporal convolution 54 or 55 for a type of bipolar cells (kernels $h^{BC}$ having time constants $\tau^{exc}$ for an excitatory cell and $\tau^{inh}$ for an inhibitory cell). In this model, the radii $r^{PR}$, $r^{HC}$ can take into account spatial integrations which in actuality are distributed all along the chain containing the three cell types. Similarly, the time constants $\tau^{exc}$, $\tau^{inh}$ can take into account temporal integrations which in actuality are distributed all along the chain containing the three cell types, possibly including the amacrine cells and ganglion cells as well. In FIG. 6, the subtractor 53 calculates the difference between signals $V^{PR}$ and $V^{HC}$ so that it is filtered temporally, and elements 56, 57 retain the positive part of signal $V^{BC}$ in order to supply the simulated excitatory or inhibitory output, $V^{ON}=V_{ON}^{exc}$ or $V_{ON}^{inh}$ of an 'ON' bipolar cell.

FIG. 6 also shows an example of modeling the behavior of amacrine cells and ganglion cells. In this example, the layer of amacrine cells receives the inhibitory signal $V_{ON}^{inh}$ from an 'ON' bipolar cell, delays it by a period D (delay unit 59), and filters it spatially with a convolution kernel 60 of radius $r^{AC}$ (for example a centered kernel, meaning with $x_0=y_0=0$). The resulting signal is an inhibitory component $V^{AC}$ sent to the layer of ganglion cells with the excitatory signal $V_{ON}^{exc}$ from a bipolar cell which, in the example in FIG. 6, is also an 'ON' cell. The layer of ganglion cells of a given type is modeled by a multiplier 62 which weights the inhibitory component $V^{AC}$ by a coefficient α, a subtractor 63 which subtracts the weighted inhibitory component $\alpha.V^{AC}$ from the excitatory signal $V_{ON}^{exc}$, a filter 64 which applies the convolution kernel $h^{GC}$, limited here to a spatial kernel of radius $r^{GC}$, and an emitter of action potentials 65 receiving the convoluted signal $V^{GC}=h^{GC}*(V_{ON}^{exc}-\alpha.V^{AC})$. Each time the voltage signal $V^{GC}$ reaches a positive threshold θ, the emitter 65 produces an action potential ("spike") in its output signal and resets the voltage signal $V^{GC}$ to zero, thus reinitializing the integration process occurring in the filtering 64.

A model such as the one represented in FIG. 6 allows reproducing the responses of certain 'ON' ganglion cells. From measurements of action potentials observed in the optic nerve and/or excitatory and inhibitory currents in response to a given stimulus (see B. Roska et al, "Parallel Processing in Retinal Ganglion Cells: How Integration of Space-Time Patterns of Excitation and Inhibition Form the Spiking Output", Journal of Neurophysiology, Vol. 95, No. 6, 2006, p. 3810-3822), an optimization process is used to select the model parameters most suitable for best reproducing the observations. In the case in FIG. 6, the parameter values are $r^{PR}$, $r^{HC}$, $\tau^{exc}$, $\tau^{inh}$, D, $r^{AC}$, α, $r^{GC}$ and θ.

Figure 7:
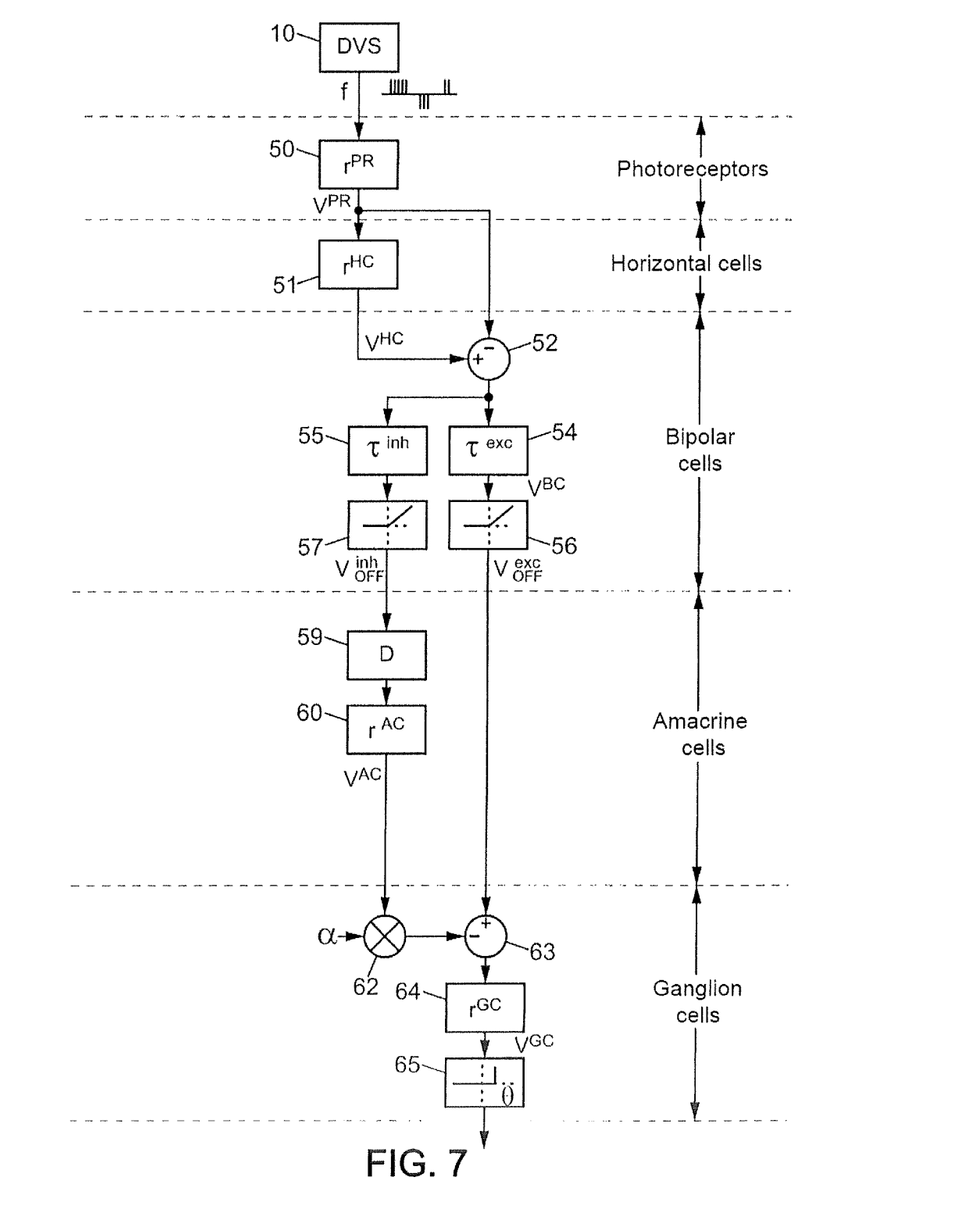

The case in FIG. 6 concerns 'ON' ganglion cells, meaning those that respond to stimuli as positive lines in the input signal. The model is easily applied to the case of 'OFF' ganglion cells, meaning those that respond to stimuli as negative lines in the input signal. The diagram can then be the one shown in FIG. 7, which is the same as the one in FIG. 6 except that the subtraction 52 between signals $V^{PR}$ and $V^{HC}$ occurring in the layer of bipolar cells has a reverse polarity to what is shown 53 in FIG. 6.

Figure 8:
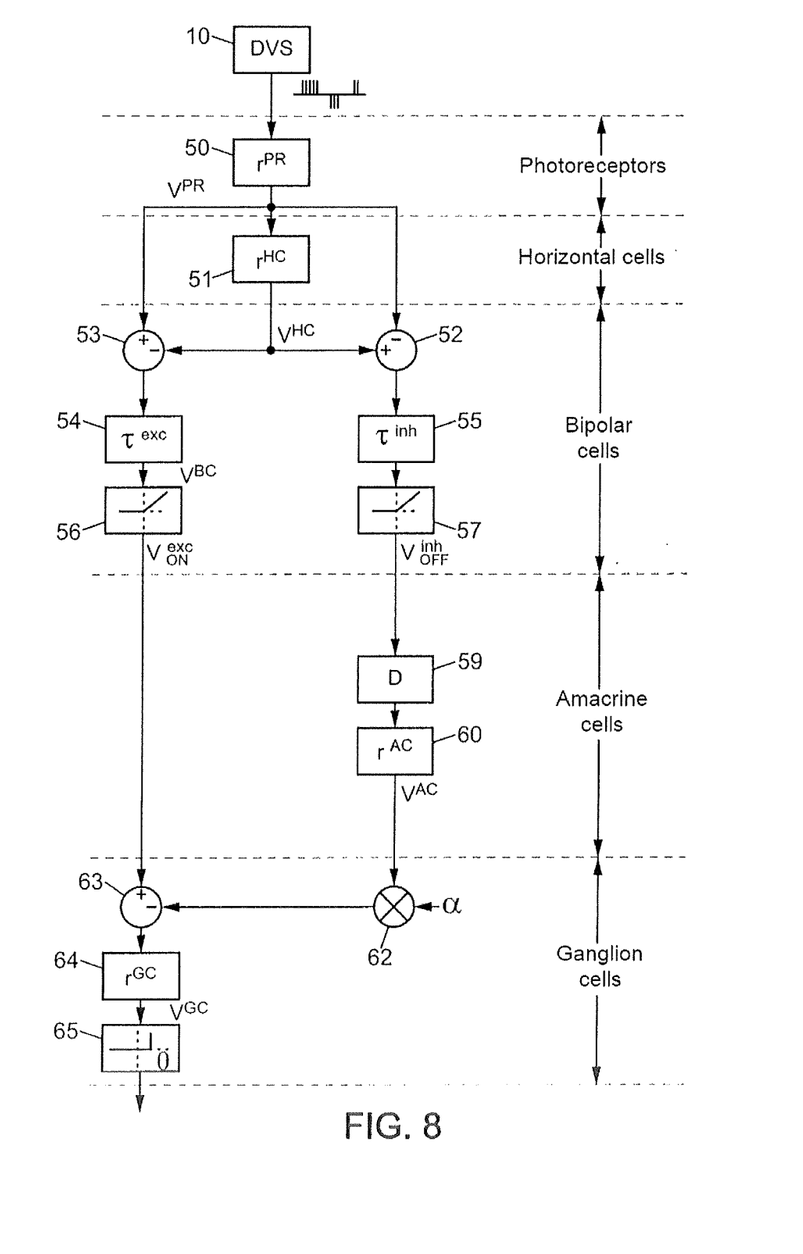

Another possible situation is that ganglion cells receive their excitatory signals $V_{ON}^{exc}$ (or $V_{OFF}^{exc}$) from 'ON' bipolar cells (or 'OFF') while their inhibitory components $V^{AC}$ are obtained from 'OFF' bipolar cells (or 'ON'). This situation is illustrated by FIG. 8 in a case of excitation by 'ON' bipolar cells and inhibition by 'OFF' bipolar cells.

Figure 9:
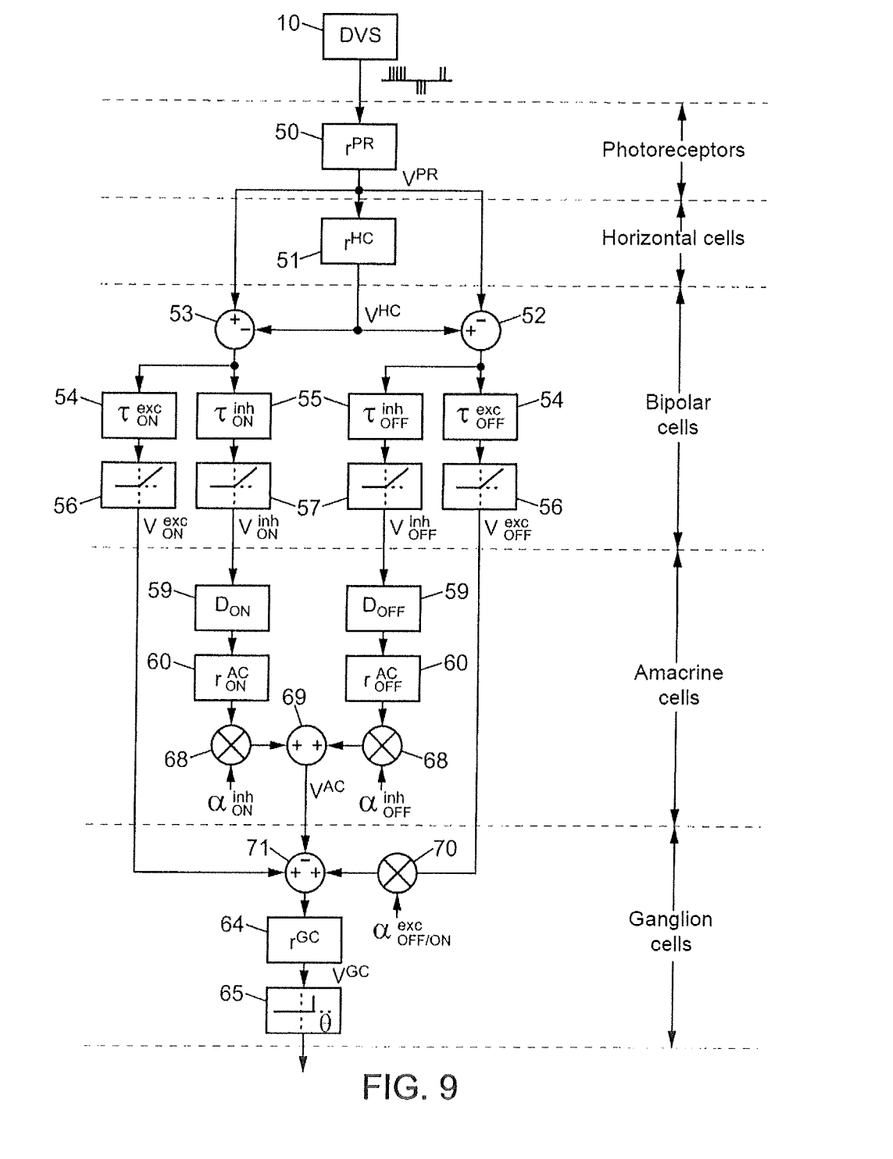

Yet another possibility, illustrated in FIG. 9, is where the ganglion cells are excited by both 'ON' and 'OFF' bipolar cells (with a relative weighting adjusted by a positive coefficient $\alpha_{OFF/ON}^{exc}$), and are inhibited by components $V^{AC}$ issuing from combinations of inhibitory signals $V_{ON}^{inh}$, $V_{OFF}^{inh}$ emitted by 'ON' and 'OFF' bipolar cells. Two families of amacrine cells are then modeled in such a channel, with different times $D_{ON}$, $D_{OFF}$ in the delay units 59 and possibly different radii of interaction $r_{ON}^{AC}$, $r_{OFF}^{AC}$ at the filters 60. The outputs from the two filters 60 are linearly combined to form the inhibitory component $V^{AC}$. In the example in FIG. 9, the combination is done using multipliers 68, which apply respective weighting factors $\alpha_{ON}^{inh}$, $\alpha_{OFF}^{inh}$ to the filtered signals of the 'ON' channel pathway and the 'OFF' pathway, and an adder 69 which produces the inhibitory component $V^{AC}$ as the sum of the filtered and weighted signals.

In the model of the layer of ganglion cells in FIG. 9, a multiplier 70 applies the weighting factor $\alpha_{OFF/ON}^{exc}$ to the excitatory signal $V_{OFF}^{exc}$ issuing from the 'OFF' bipolar cell. The excitatory and inhibitory components are combined in 71 to supply the input $V_{ON}^{exc}+\alpha_{OFF/ON}^{exc}.V_{OFF}^{exc}-V^{AC}$ for the spatial filter 64. The values of the weighting factors $\alpha_{OFF/ON}^{exc}$, $\alpha_{ON}^{inh}$, $\alpha_{OFF}^{inh}$ allow adjusting the relative excitatory and inhibitory levels from the various bipolar cells involved.

In a variant of the diagram in FIG. 9, the input for the spatial filter 64 is not $V_{ON}^{exc}+\alpha_{OFF/ON}^{exc}.V_{OFF}^{exc}-V^{AC}$ but $\alpha_{ON/OFF}^{exc}.V_{ON}^{exc}+V_{OFF}^{exc}-V^{AC}$. The factor $\alpha_{OFF/ON}^{exc}$ or $\alpha_{ON/OFF}^{exc}$ is positive or zero. It can be constrained to be zero, in which case the ganglion cells are excited by only one type of bipolar cell and inhibited by two types of bipolar cell via the amacrine cells.

For ganglion cells that are part of other information pathways, other excitatory schemes involving differing parameters can be added to the model.

From the AER signal from the DVS sensor 10, a model such as the one illustrated in FIGS. 5-9 allows appropriately reproducing, by optimizing the model parameters, the ten types of responses in rodents described in the aforementioned article by B. Roska, et al. This demonstrates the ability of the method to provide appropriate stimulation of retinal nerve cells.

For direction-selective ganglion cells, the model can be enriched to include an offset $x_0$, $y_0$ in the spatial filtering kernel 60 applied in the layer, representing the processing performed by the amacrine cells. This off-center kernel, combined with the delay D applied by these amacrine cells, reflects a directionality of the stimuli along the orientation of the shift $x_0$, $y_0$.

When the prosthesis is implanted epiretinally, it influences the electrical potential of ganglion cells. The control signal S delivered by the signal processing unit 30 of FIG. 1 can then be the signal produced by the action potential emitter 65 represented in one of FIGS. 6-9. The type of ganglion cells to be stimulated and the corresponding modeling scheme can be selected for a given patient by administering psychophysical tests to find the control mode that provides the best perceptual results. It is also possible to make adjustments to some of the model parameters during such tests. An alternative implantation of the prosthesis is on the cortex and the lateral geniculate nucleus (which is between the retina and the cortex). In the latter case, signals similar to those mentioned above for epiretinal stimulation for example could be applied to the prosthesis.

If the prosthesis is implanted subretinally, it influences the electric potential of bipolar cells. In this case, the control signal S delivered by the processing unit 30 of FIG. 1 can be the signal $V_{ON}^{exc}$, $V_{OFF}^{exc}$, $V_{ON}^{inh}$, $V_{OFF}^{inh}$ produced by an element 56, 57 involved in the modeling of bipolar cells. Again, the type of bipolar cells to be stimulated and the corresponding modeling scheme can be selected for a given patient by administering psychophysical tests.

The spatial resolution of the pixel zones in the prosthesis 20 is not necessarily the same as that of the pixels in the DVS sensor 10. A spatial resampling of the signal may therefore occur in the transformation of the input signal f to a control signal S. In the typical case where the resolution is lower at the prosthesis 20 than at the sensor 10, the spatial sub-sampling can occur during the final spatial filtering operation performed in the transformation.

The visual aid device 20 can be a device other than a prosthesis which electrically excites cells of the visual system. In the case of a visual orthosis, the converter may correspond to a matrix of light-emitting elements (for example LED, MicroOLED, LCD) which takes signals from different signal integration levels to produce a visual representation.

Orthoses controlled in this way can be used in conjunction with gene therapy, which is one of the treatment strategies for degenerative diseases of photoreceptors. One form of gene therapy consists of expressing photosensitive ion channels or photosensitive carriers in the remaining cells of the retina (photoreceptors having lost their photosensitivity, bipolar, amacrine and ganglion cells). This genetic modification 'creates' new photoreceptors that can be excited by light. However, their sensitivity is low compared to rods and cones. On the other hand, depending on the type of cell in question, the visual information can be processed similarly to prostheses that use electrical stimulation. This is why it is useful in such cases to use a visual aid device that creates a stimulation which is no longer electrical but light-based and which requires the same type of processing.

The embodiments described above are illustrative of the invention. Various modifications can be made to them without departing from the scope of the invention as set forth in the appended claims. In particular, the method is not limited to the mathematical expressions, or more generally to the modeling, referred to above in order to develop the control signals S for the visual aid device.

The invention claimed is:

1. A method of controlling a visual aid device, comprising:
   receiving an input signal representative of a scene to be viewed, the input signal comprising, for each pixel in a matrix of pixels, an event-based asynchronous signal sequence obtained as a function of variations of light relating to the pixel in the scene;
   transforming the input signal spatially within the matrix of pixels and temporally along the event-based asynchronous signal sequences to generate respective control signals for pixel zones of the visual aid device; and
   applying the control signals to the visual aid device,
   wherein the event-based asynchronous signal sequence for a pixel comprises a sequence of pulses temporally positioned as a function of the light variations relating to the pixel,
   wherein transforming the input signal to generate the control signals comprises:
   obtaining a first signal resulting from two spatial filtering operations with filtering kernels of different sizes, calculation of a difference between results of the two spatial filtering operations, and a temporal filtering operation on the difference; and
   obtaining a second signal of zero value if the first signal has a value of a specific sign, and of the same absolute value as the first signal otherwise.

2. The method of claim 1, wherein the vision aid device comprises a subretinal visual prosthesis, and the control signals applied to the visual prosthesis are generated from said second signal.

3. The method of claim 1, wherein the visual aid device comprises a matrix of light-emitting elements and the control signals applied to said matrix are generated from said second signal.

4. The method of claim 1, wherein at least a first excitatory signal and a first inhibitory signal are obtained with respective time constants for the temporal filtering operation on the difference, and wherein at least a second excitatory signal and a second inhibitory signal are respectively obtained from the first excitatory and inhibitory signals.

5. The method of claim 4, wherein transforming the input signal to generate the control signals further comprises:
   obtaining a third signal resulting from a spatial filtering operation on the difference between the second excitatory signal and an inhibitory component derived from the second inhibitory signal; and
   when the third signal for a given pixel zone of the visual aid device exceeds a predetermined threshold value, inserting a pulse into the control signal intended for said pixel zone and resetting the third signal for said pixel zone to zero.

6. The method of claim 5, wherein derivation of the inhibitory component from the second inhibitory signal comprises the application of a predetermined delay and a spatial filtering operation.

7. The method of claim 6, wherein the spatial filtering operation in the derivation of the inhibitory component uses an off-center filtering kernel.

8. The method of claim 4, wherein the second excitatory and inhibitory signals are obtained for a first channel and for a second channel with temporal filtering operations at respective time constants, and wherein transforming the input signal to generate the control signals further comprises:
 obtaining a third signal resulting from a spatial filtering operation on the difference between a linear combination of the second excitatory signals for the first and second channels and an inhibitory component derived from the second inhibitory signals for the first and second channels; and
 when the third signal for a given pixel zone of the visual aid device exceeds a given threshold value, inserting a pulse into the control signal for said pixel zone and resetting the third signal for said pixel zone to zero.

9. The method of claim 8, wherein derivation of the inhibitory component from the second inhibitory signals comprises the application of respective delays to the second inhibitory signals for the first and second channels, a spatial filtering operation on the delayed second inhibitory signals, and calculation of a linear combination of delayed and filtered second inhibitory signals.

10. The method of claim 5, wherein the visual aid device comprises a visual prosthesis in an epiretinal or cortical position or on the lateral geniculate body, and the control signals applied to the visual prosthesis are generated from said third signal.

11. The method of claim 5, wherein the visual aid device includes a matrix of light-emitting elements and the control signals applied to this matrix are generated from said third signal.

12. The method of claim 1, wherein transforming the input signal in order to generate the control signals is carried out using an artificial neural network.

13. A device for processing signals for controlling a visual aid device, comprising:
 an input for receiving an input signal representative of a scene to be viewed, the input signal comprising, for each pixel in a matrix of pixels, an event-based asynchronous signal sequence obtained as a function of variations of light relating to the pixel in the scene;
 an output for supplying the control signals for the visual aid device; and
 a processing circuit for generating the control signals, respective control signals being generated for pixel zones of the visual aid device by transforming the input signal spatially within the matrix of pixels and temporally along the event-based asynchronous signal sequences,
 wherein the event-based asynchronous signal sequence for a pixel comprises a sequence of pulses temporally positioned as a function of the light variations relating to the pixel,
 wherein the processing circuit is configured for transforming the input signal by:
 obtaining a first signal resulting from two spatial filtering operations with filtering kernels of different sizes, calculation of a difference between results of the two spatial filtering operations, and a temporal filtering operation on the difference; and
 obtaining a second signal of zero value if the first signal has a value of a specific sign, and of the same absolute value as the first signal otherwise.

14. The device of claim 13, wherein at least a first excitatory signal and a first inhibitory signal are obtained with respective time constants for the temporal filtering operation on the difference, and wherein at least a second excitatory signal and a second inhibitory signal are respectively obtained from the first excitatory and inhibitory signals.

15. The device of claim 14, wherein the processing circuit is further configured for transforming the input signal by:
 obtaining a third signal resulting from a spatial filtering operation on the difference between the second excitatory signal and an inhibitory component derived from the second inhibitory signal; and
 when the third signal for a given pixel zone of the visual aid device exceeds a predetermined threshold value, inserting a pulse into the control signal intended for said pixel zone and resetting the third signal for said pixel zone to zero.

16. The device of claim 14, wherein the second excitatory and inhibitory signals are obtained for a first channel and for a second channel with temporal filtering operations at respective time constants, and wherein the processing circuit is further configured for transforming the input signal by:
 obtaining a third signal resulting from a spatial filtering operation on the difference between a linear combination of the second excitatory signals for the first and second channels and an inhibitory component derived from the second inhibitory signals for the first and second channels; and
 when the third signal for a given pixel zone of the visual aid device exceeds a given threshold value, inserting a pulse into the control signal for said pixel zone and resetting the third signal for said pixel zone to zero.

17. The device of claim 13, wherein the processing circuit comprises an artificial neural network.

18. The method of claim 8, wherein the visual aid device comprises a visual prosthesis in an epiretinal or cortical position or on the lateral geniculate body, and the control signals applied to the visual prosthesis are generated from said third signal.

19. The method of claim 8, wherein the visual aid device includes a matrix of light-emitting elements and the control signals applied to this matrix are generated from said third signal.

* * * * *